US012784912B2

(12) United States Patent
Rao

(10) Patent No.: US 12,784,912 B2
(45) **Date of Patent: *Nov. 3, 2026**

(54) METHOD OF IMPLEMENTING AN ARTIFICIAL INTELLIGENCE BASED IMAGING PLATFORM FOR NEUROLOGICAL ANALYSIS

(71) Applicant: SCA Robotics, Moraga, CA (US)

(72) Inventor: Rob K. Rao, Moraga, CA (US)

(73) Assignee: SCA ROBOTICS, Moraga, CA (US)

( * ) Notice: Subject to any disclaimer, the term of this patent is extended or adjusted under 35 U.S.C. 154(b) by 489 days.

This patent is subject to a terminal disclaimer.

(21) Appl. No.: 18/544,046

(22) Filed: Dec. 18, 2023

(65) Prior Publication Data

US 2024/0194345 A1 Jun. 13, 2024

Related U.S. Application Data

(62) Division of application No. 18/074,396, filed on Dec. 2, 2022, now Pat. No. 11,848,105, which is a division (Continued)

(51) Int. Cl.
*G16H 50/20* (2018.01)
*A61B 5/00* (2006.01)

(Continued)

(52) U.S. Cl.
CPC ........... *G16H 50/20* (2018.01); *A61B 5/0042* (2013.01); *A61B 5/055* (2013.01); *A61B 5/7267* (2013.01);

(Continued)

(58) Field of Classification Search
CPC .......... G16H 50/20; G01R 33/00; A61B 5/00; G06N 3/0464; G06N 3/09; G06N 3/00
See application file for complete search history.

(56) References Cited

U.S. PATENT DOCUMENTS 8,953,858 B2 2/2015 Becker et al.
9,922,272 B2 3/2018 Cheng et al.

(Continued)

OTHER PUBLICATIONS

Moeskops et al. "Automatic Segmentation of MR Brain Images With a Convolutional Neural Network," in IEEE Transactions on Medical Imaging, vol. 35, No. 5, pp. 1252-1261, May 2016, doi: 10.1109/TMI.2016.2548501. (Year: 2016).*

(Continued)

*Primary Examiner* — Anhtuan T Nguyen
*Assistant Examiner* — Younhee Choi
(74) *Attorney, Agent, or Firm* — Blynn L. Shideler; Krisanne Shideler; BLK Law Group

(57) ABSTRACT

An artificial neural network based platform uses a validated multilayer convolutional network for neurological analysis configured for segmenting data sets of neurological scans of a specific given patient. The validated multilayer convolutional network of the platform includes classification of neurological tissue within classification voxels of at least one patient data set by the validated multilayer convolutional network for neurological analysis with each classification voxel of the at least one patient data set assigned a label, wherein the implementing the validated multilayer convolutional network includes at least one of i) mapping neurologic tissue or ii) mapping of a neurological tumor of a patient.

16 Claims, 5 Drawing Sheets

Related U.S. Application Data of application No. 16/515,610, filed on Jul. 18, 2019, now Pat. No. 11,521,742.

(60) Provisional application No. 62/816,954, filed on Mar. 12, 2019, provisional application No. 62/699,974, filed on Jul. 18, 2018.

(51) Int. Cl.

| | |
|---|---|
| ***A61B 5/055*** | (2006.01) |
| ***G01R 33/56*** | (2006.01) |
| ***G06N 3/08*** | (2023.01) |
| ***G06V 10/26*** | (2022.01) |
| ***G06V 10/44*** | (2022.01) |
| ***G06V 10/764*** | (2022.01) |
| ***G06V 10/82*** | (2022.01) |

(52) U.S. Cl.

CPC ........... *G01R 33/5608* (2013.01); *G06N 3/08* (2013.01); *G06V 10/26* (2022.01); *G06V 10/454* (2022.01); *G06V 10/764* (2022.01); *G06V 10/82* (2022.01)

(56) References Cited

U.S. PATENT DOCUMENTS

| | | | |
|---|---|---|---|
| 10,825,168 | B2 | 11/2020 | Tegzes |
| 11,234,666 | B2 | 2/2022 | Chan |
| 2018/0008187 | A1 | 1/2018 | Chou et al. |
| 2020/0193594 | A1 | 6/2020 | Georgescu |
| 2020/0214619 | A1 | 7/2020 | Leng |
| 2021/0035296 | A1 | 2/2021 | Mahrooghy |

OTHER PUBLICATIONS

Mehta et al. "BrainSegNet: a convolutional neural network architecture for automated segmentation of human brain structures," Journal of Medical Imaging 4(2), 024003 (Apr. 20, 2017). Doi: 10.1117/1.JMI.4.2.024003. (Year: 2017).*

Rao et al. "Contusion segmentation from subjects with Traumatic Brain Injury: A random forest framework," 2014 IEEE 11th International Symposium on Biomedical Imaging (ISBI), Beijing, China, 2014, pp. 333-336, doi: 10.1109/ISBI.2014.6867876. (Year: 2014).*

* cited by examiner

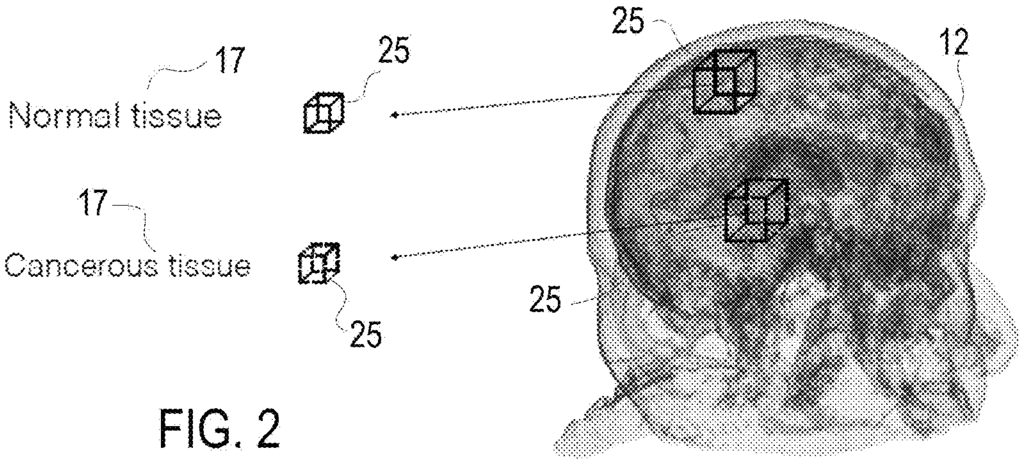
FIG. 2
FIG. 3A
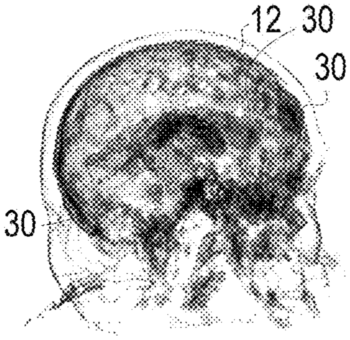
FIG. 3B
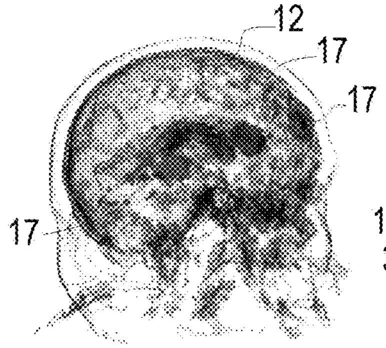
FIG. 3C
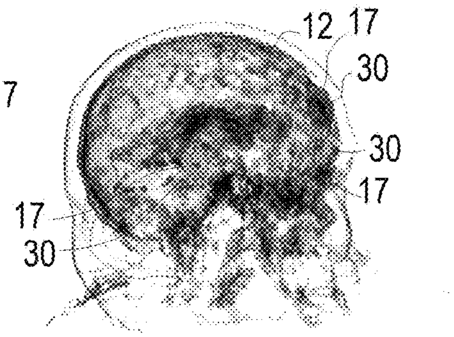

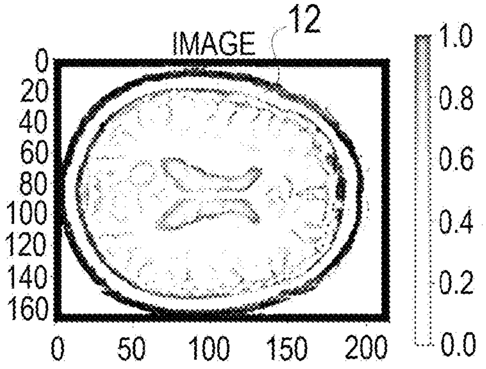
FIG. 4A
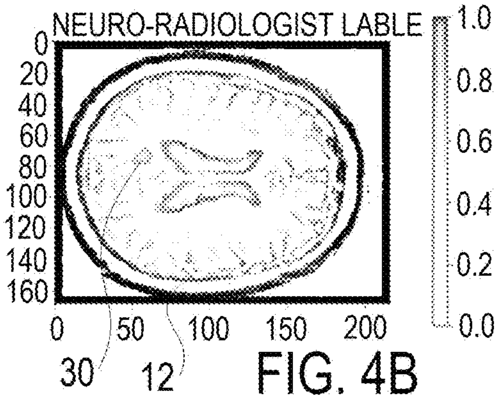
FIG. 4B
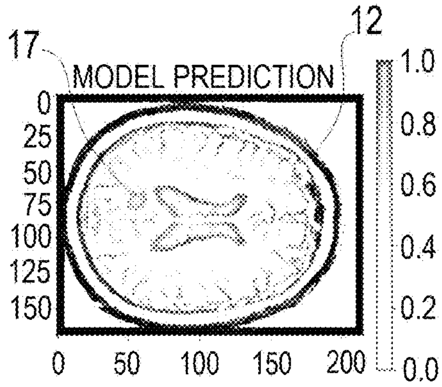
FIG. 4C
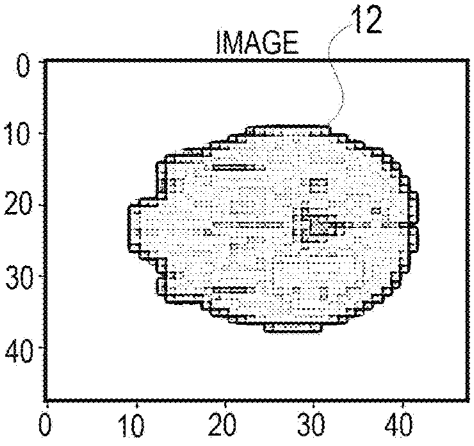
FIG. 5A
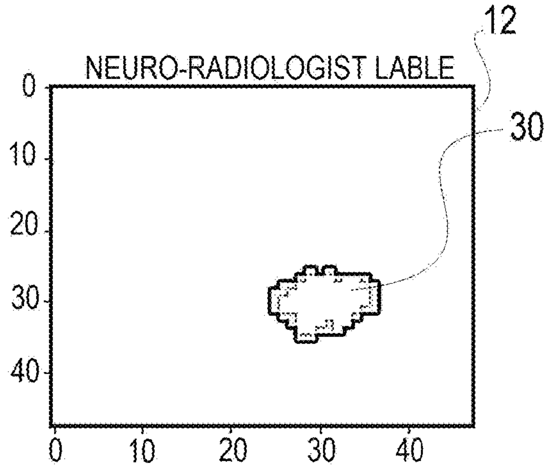
FIG. 5B
FIG. 5C
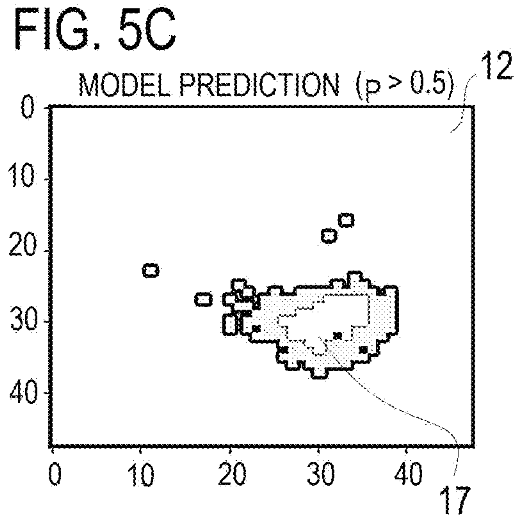

METHOD OF IMPLEMENTING AN ARTIFICIAL INTELLIGENCE BASED IMAGING PLATFORM FOR NEUROLOGICAL ANALYSIS

CROSS-REFERENCE TO RELATED APPLICATIONS

This application is a divisional application of U.S. patent application Ser. No. 18/074,396, filed Dec. 2, 2022 and published Apr. 6, 2023 as publication number US2023-010943 and which issued as U.S. Pat. No. 11,848,105, which application and publication are incorporated herein by reference.

U.S. patent application Ser. No. 18/074,396 is a divisional application of U.S. patent application Ser. No. 16/515,610 filed Jul. 18, 2019 which published Jan. 23, 2020 as publication 2020-0027561 and issued as U.S. Pat. No. 11,521,742 which patent, publication and application are incorporated herein by reference.

U.S. patent application Ser. No. 16/515,610 claims the benefit of provisional patent application Ser. No. 62/816,954 filed Mar. 12, 2019 titled "Precision Medical Treatment Predictive Modeling Platform for Diabetes, Neurological and Cardiopulmonary Analysis" which is incorporated herein by reference.

U.S. patent application Ser. No. 16/515,610 claims the benefit of provisional patent application Ser. No. 62/699,974 filed Jul. 18, 2018 titled "Precision Medical Treatment Predictive Modeling Platform for Diabetes, Neurological and Cardiopulmonary Analysis" which is incorporated herein by reference.

BACKGROUND OF THE INVENTION

1. Field of the Invention

The present invention relates to methods of implementing an artificial intelligence based diabetes precision medical treatment predictive modeling platform.

2. Background Information

Neurological tumors within the meaning of this application reference tumors relating to the neurologic system, most commonly brain tumors and spinal cord tumors. Brain tumors will be most illustrative of the present invention and the following discussion concentrates on these solely for illustration. A brain tumor is an abnormal growth of cells inside the brain or skull; some are benign, others malignant. Tumors can grow from the brain tissue itself, known as primary brain tumors, or cancer from elsewhere in the body can spread to the brain, known as a metastatic or secondary brain tumor. Treatment options vary depending on the tumor type, size and location. Treatment goals may be curative or focus on relieving symptoms. Many of the 120 types of brain tumors can be successfully treated is discovered early.

Normal brain cells grow in a controlled manner as new cells replace old or damaged ones. For reasons not fully understood, tumor cells reproduce uncontrollably. A primary brain tumor is an abnormal growth that starts in the brain and usually does not spread to other parts of the body. Primary brain tumors may be benign or malignant. A benign brain tumor grows slowly, has distinct boundaries, and rarely spreads. Although its cells are not malignant, benign tumors can be life threatening if located in a vital area. A malignant brain tumor grows quickly, has irregular boundaries, and spreads to nearby brain areas. Although they are often called brain cancer, malignant brain tumors do not fit the definition of cancer because they do not spread to organs outside the brain and spine.

Metastatic or secondary brain tumors begin as cancer elsewhere in the body and spread to the brain. Metastatic brain tumors form when cancer cells are carried in the blood stream. The most common cancers that spread to the brain are lung and breast.

Whether a brain tumor is benign, malignant, or metastatic, all are potentially life-threatening. Enclosed within the bony skull, the brain cannot expand to make room for a growing mass. As a result, the tumor compresses and displaces normal brain tissue. Some brain tumors cause a blockage of cerebrospinal fluid that flows around and through the brain. This blockage increases intracranial pressure and can enlarge the ventricles, known as hydrocephalus. Some brain tumors cause swelling, known as edema. Size, pressure, and swelling all create "mass effect," which cause many of the symptoms experienced by the patient.

Medical imaging based screening techniques have long been used for the early detection of cancer and the scientific community considers that they play a major role in the reduction in mortality for certain cancer types. Researchers as Stanford University in 2017 demonstrated the potential of deep convolutional neural networks algorithms for dermatologist-level classification of skin cancer, which is primarily diagnosed visually. The largest ever dataset, comprising 129,450 clinical images and consisting of 2,032 different diseases, was used to train and test a convolutional neural network algorithm. The result was a performance comparable with that of each of the 21 board-certified dermatologists when trying to identify both the most common and the deadliest skin cancer.

In 2014, Israeli startup Zebra Medical Vision has taken began to develop a cloud based radiology offering that includes their application of machine learning that identifies abnormalities in CT scans. In 2016, Zebra Medical Vision announced the availability of algorithms that automatically detect low bone mineral density, breast cancer, fatty liver, coronary artery calcium, and emphysema.

In 2016, International Business Machines Corporation partnered with numerous health systems, imaging technology companies, and academic medical centers to train Watson AI, its cognitive computer, to read medical images. This more broadly based collaboration is focusing on cancer, cardiovascular disease, eye health, and diabetes. See *Artificial Intelligence with Deep Learning Technology Looks into Diabetic Retinopathy Screening* Tien Yin Wong, MD, PhD; Neil M. Bressler, MD *JAMA.* 2016.

Infervision, a Beijing-based company, uses machine learning algorithms and computer vision methods to support lung cancer diagnosis. The product is promoted as a "second pair of eyes" for the radiologists and it can identify more than 20 different cardiothoracic lesions, and can be used in physical examinations to screen for lung cancer characteristics and to quickly locate lesions.

India's Niramai has used a high resolution thermal sensing device and a cloud hosted analytics solution to analyze thermal images for reliable, early and accurate breast cancer screening. Early results, from data of 300 patients collected in two hospitals and one diagnostic center, demonstrate high accuracy, however these results remains to be validated in large-scale pilot studies. Similarly in 2017, Google announced that it had created a neural network that could analyze medical images and identify breast tumors with a greater degree of accuracy than human pathologists. The study revealed that the company, using its GoogLeNet AI, reviewed thousands of medical images supplied by a Dutch university and was able to identify malignant tumors in breast cancer images with an 89% accuracy rate, compared to 73% for its human counterparts.

California-based Arterys working with GE Healthcare plans to take MRI images and use cloud-based GPUs to produce 3D animations of the heart which it then proposed to analyze for defects.

In 2015, New York-based Imagen Technologies announced the development of AI capable of detecting pathologies and early disease identification within medical images.

Founded in 2014, Maryland-based Proscia is to develop a pathology cloud platform that uses image analysis and big data analysis to provide organizations a platform to work with whole slide images. The platform intends to make all the images anonymous and then begin analyzing them using artificial intelligence. Pathologists are intended to receive "suggestions" as to what sort of information can be gleaned from the images they upload.

California based Bay Labs, in 2016, combined deep learning artificial intelligence based algorithm with cardiovascular ultrasound imaging to help in the diagnosis and management of heart disease, the leading cause of death in the world.

Issued in 2015, U.S. Pat. No. 8,953,858, which is incorporated herein by reference, discloses a system or platform for retrieving and processing medical diagnostic images using a picture analysis prioritization visualization and reporting system ("PAPVR system") to determine whether one or more images from an image database is of medical interest to a reviewing physician, and to determine whether one or more of the images is representative of the images, and to provide the one or more images to a display and analysis system for review by a reviewing physician. The PAPVR system is configured to provide a "key Image" that is representative of the images.

Issued in 2018, U.S. Pat. No. 9,922,272, which is incorporated herein by reference, discloses machine learning for multimodal image data. A similarity metric for multi-modal images is provided using the corresponding states of pairs of image patches to generate a classification setting for each pair. The classification settings are used to train a deep neural network via supervised learning. A multi-modal stacked de-noising auto encoder (SDAE) is used to pre-train the neural network. A continuous and smooth similarity metric is constructed based on the output of the neural network before activation in the last layer. The trained similarity metric may be used to improve the results of image fusion.

Published in 2018, U.S. Patent Application 2018-0008187, which is incorporated herein by reference, from Sony Corporation discloses a system implementing an AI based model for joint brain tumor and cortex reconstruction from MRI datasets intended to be trained "on-the-fly" to yield tumor and cortical surface reconstruction for diagnostic and surgical guidance.

Artificial intelligence is incredible tool being used across numerous systems. The industry and the applicant believe there remains a need to efficiently add these resources to medicine and more particularly to predicting models for neurological analysis. This view is shared and expressed by the Radiological Society of North America (RSNA), the American College of Radiology (ACR) and The Academy for Radiology and Biomedical Imaging Research (The Academy). In August 2018, a workshop was held at the National Institutes of Health (NIH) in Bethesda, Md., to explore the future of artificial intelligence (AI) in medical imaging. The workshop was co-sponsored by NIH, RSNA, ACR and The Academy. The organizers aimed to foster collaboration in applications for diagnostic medical imaging, identify knowledge gaps and develop a roadmap to prioritize research needs. The group's research roadmap was published as a special report in the journal Radiology on Apr. 16, 2019. In addition to establishing image labeling and annotation methods for facilitating model development in the field, the report restated the need for the development of novel pre-trained model architectures, tailored for clinical imaging data, along with methods for distributed training that reduce the need for data exchange between institutions.

SUMMARY OF THE INVENTION

One aspect of the present invention provides a method of implementing a diabetes predictive modeling platform utilizing artificial intelligence based analysis predicting glucose levels comprising the steps of: providing an artificial neural network for predicting glucose levels configured predicating glucose levels of a given patient; supervised learning of the platform based upon a supervised learning data set including at least historic Glucose measurements, Insulin treatment history, and history of onset of hypoglycemic symptoms for at least one patient for developing a platform model for predicting glucose levels of any patient; validating the platform model for predicting glucose levels of any patient by providing validating data set comprising Glucose measurements, Insulin treatment history, and history of onset of hypoglycemic symptoms for at least one patient with each patient of the validation data set having a predetermined ground truth glucose levels to be predicted by the platform model; and implementing the platform model for predicting glucose levels on a specific given patient data set by the artificial neural network to predict the glucose levels of the specific given patient.

One aspect of the present invention provides an artificial neural network based platform for predicting glucose levels of a specific given patient, comprising a platform model for predicting glucose levels of any patient developed under supervised learning based upon a supervised learning data set including at least historic glucose measurements, insulin treatment history, and history of onset of hypoglycemic symptoms for at least one patient; wherein the platform model has been validated for predicting glucose levels of any patient by providing validating data set comprising glucose measurements, insulin treatment history, and history of onset of hypoglycemic symptoms for at least one patient with each patient of the validation data set having a predetermined ground truth glucose levels to be predicted by the platform model; and wherein the platform model is configured for predicting glucose levels on a specific given patient data set by the artificial neural network to predict the glucose levels of the specific given patient.

These and other advantages of the present invention will be clarified in the brief description of the preferred embodiment taken together with the drawings in which like reference numerals represent like elements throughout.

BRIEF DESCRIPTION OF THE SEVERAL VIEWS OF THE DRAWING

FIG. 2 is an exploded schematic view of a scan used by the artificial intelligence based neuroradiology platform for neurological tumor identification and classification voxels on the scan and assigned labels for the classification voxels in accordance with one aspect of the present invention;

FIG. 3A is schematic view of a training scan with known classification labels for training the artificial intelligence based neuroradiology platform for neurological tumor identification of the present invention;

FIG. 3B is schematic view of a scan associated with training scan of FIG. 3A with predicted classification labels by the artificial intelligence based neuroradiology platform for neurological tumor identification of the present invention;

FIG. 3C is a superimposed view of FIGS. 3A and 3B;

FIGS. 4A, 5A and 6A are schematic views of distinct training scans for training the artificial intelligence based neuroradiology platform for neurological tumor identification of the present invention;

FIGS. 4B, 5B and 6B are schematic views of the training scans of FIGS. 4A, 5A and 6A, respectively, with added known classification labels for training the artificial intelligence based neuroradiology platform for neurological tumor identification of the present invention;

FIGS. 4C, 5C and 6C are schematic view of scans associated with training scan of FIGS. 4A, 5A and 6A, respectively, with predicted classification labels by the artificial intelligence based neuroradiology platform for neurological tumor identification of the present invention;

DESCRIPTION OF THE PREFFERED EMBODIMENTS

The present invention provides effective and efficient precision artificial intelligence based neuroradiology platform 10 for neurological tumor identification and for T-Cell therapy initiation and tracking and related precision medical treatment predictive modeling platforms.

Artificial intelligence (AI) has several working definitions and can be efficiently defined herein as the simulation of human intelligence processes by machines, especially computer systems. These processes include learning (the acquisition of information and rules for using the information), reasoning (using rules to reach approximate or definite conclusions) and self-correction. Machine learning is a subset of AI, and can be categorized by its ability to modify itself when exposed to more data; i.e. machine learning is dynamic and does not require human intervention to make certain changes. Deep learning is a subset of machine learning, and herein it is referring to deep artificial neural networks.

Deep in this context refers to the number of layers in a neural network. A shallow network has one so-called “hidden layer”, and a deep network has more than one. Multiple hidden layers allow deep neural networks to learn features of the data in a so-called feature hierarchy, because simple features (e.g. two pixels) recombine from one layer to the next, to form more complex features (e.g. a line). Nets with many layers pass input data (features) through more mathematical operations than nets with few layers, and are therefore more computationally intensive to train. Computational intensively is one of the hallmarks of deep learning.

Artificial neural networks are a set of algorithms, modeled loosely after the human brain, that are designed to recognize patterns. Artificial neural networks interpret sensory data through a kind of machine perception, labeling or clustering raw input. The patterns they recognize are numerical, contained in vectors, into which all real-world data, be it images, sound, text or time series, must be translated. Artificial neural networks generally help cluster and classify and can be thought of generally as a clustering and classification layer on top of the data that is stored and managed. Generally, artificial neural networks help to group unlabeled data according to similarities among the example inputs, and they classify data when they have a dataset to train upon. Artificial neural networks can also extract features that are fed to other algorithms for clustering and classification; so deep neural networks may be considered as components of larger machine-learning applications involving algorithms for reinforcement learning, classification and regression.

Figure 1:
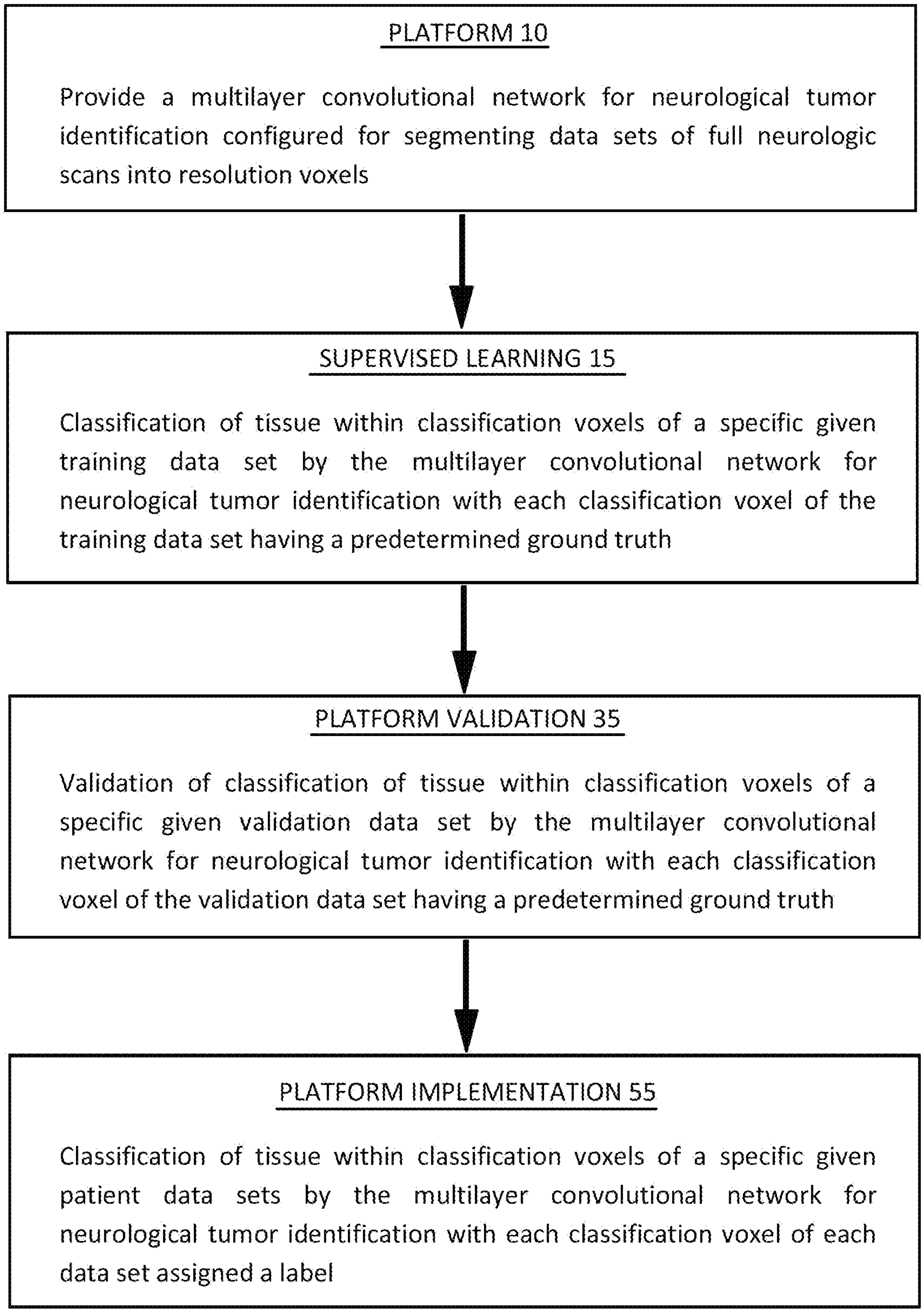
FIG. 1 is a schematic flowchart of the method of implementing an artificial intelligence based neuroradiology platform for neurological tumor identification in accordance with the present invention.

The present invention provides an artificial intelligence based neuroradiology platform 10 for neurological tumor identification. FIG. 1 is a schematic flowchart of the method of implementing an artificial intelligence based neuroradiology platform 10 for neurological tumor identification in accordance with the present invention. The platform 10 is a deep artificial neural network and may be accurately described as a 3D multilayer convolutional network. The platform 10 essentially reads medical images or scans 12, similar to radiologists, using the same rules, by identifying patterns. The platform 10 is trained, as described below using a number of known exams to allow the platform 10 to determine what normal anatomy looks like on magnetic resonance imaging (MRI) scans 12 and to allow the platform 10 to accurately identify anomalies on the scans 12.

The platform 10 formed by the multilayer convolutional network for neurological tumor identification is configured for segmenting data sets of full neurologic scans 12 into resolution voxels. The phrase full neurologic scans means a complete scan (CT, MRI, PET, etc.) of the neurologic region of interest, e.g., the brain or spine sufficient to form a 3D representation of the structure. The brain tumor being more prevalent and thus modelled more frequently, the following representations of the present invention elaborates using brain (MRI) scans 12. Further, conventional structural MRI remains the standard of care and the platform 10 will be generally be explained using MRI data inputs or scans 12.

A voxel, generally, is one of an array of elements of volume that constitute a notional three-dimensional space, especially each of an array of discrete elements into which a representation of a three-dimensional object is divided. A voxel, in general represents a value on a regular grid in three-dimensional space. As with pixels in a bitmap, voxels themselves do not typically have their position (their coordinates) explicitly encoded along with their values. Instead, the position of a voxel is inferred based upon its position relative to other voxels (i.e., its position in the data structure that makes up a single volumetric image). The phrase “resolution voxel” references the smallest volumetric region that the platform 10 can segment the data from a scan 12 into for classification, which in this case can be a cube of 1 mm per side. The data from any data set is generally cropped to the region of interest (e.g., the image within the skull or within the spine), and the data segmented into the resolution voxels for processing and classification.

The structure of a multilayer convolutional network of platform 10 is generally known to those in the artificial intelligence field and the rules governing the classification scheme of platform 10 are those that used by radiologists, or the rules used to train radiologists. A brief overview of MRI imaging for brain tumor identification by radiologists may clarify the details of the platform 10.

Despite the myriad refinements in advanced imaging techniques over the past decades, conventional structural MRI remains the standard of care imaging method for neuro-oncologic practice, and the platform 10 uses MRI data or scans 12, although an analogous platform can be created for other scan types such as CT or the like. Current consensus recommendations for a standardized brain tumor MRI protocol are the following: 3-dimensional (3-D) T1, axial fluid-attenuated inversion recovery (FLAIR), axial diffusion-weighted imaging (DWI), axial gadolinium contrast-enhanced T2, and 3-D gadolinium contrast-enhanced T1, performed on a minimum 1.5 tesla MRI system. See Ellingson B M, Bendszus M, Boxerman J et al. *Consensus recommendations for a standardized Brain Tumor Imaging Protocol in clinical trials*. Neuro Oncol. 2015; 17(9):1188-1198. If 3-D sequences cannot be performed to create the full scans 12 needed for the platform 10 due to time constraints or technical limitations, 2-D sequences (spaced less than or equal to the width of a resolution voxel) can be substituted that are "stitched" together to form the 3D imaging.

The structural sequences (T2-weighted, FLAIR, and pre- and postcontrast T1-weighted) generally can provide the primary foundation of an MRI examination for a full scan 12 for the platform 10. Specific pre-surgical sequences such as high-resolution isovolumetric 3-D T2-weighted and post-contrast 3-D T1 spoiled gradient recalled echo imaging can be obtained with fiducial markers for intraoperative navigation or with a head frame for stereotactic radio-surgical planning. See Willems P W A, van der Sprenkel J W B, Tulleken C A F, Viergever M A, Taphoorn M J B. *Neuronavigation and surgery of intracerebral tumours*. J Neurol. 2006; 253(9):1123-1136. See also Saconn P A, Shaw E G, Chan M D et al. Use of 3.0-*T MRI for stereotactic radiosurgery planning for treatment of brain metastases: a single-institution retrospective review*. Int J Radiat Oncol Biol Phys. 2010; 78 (4):1142-1146.

In addition to conventional structural sequences, DWI and T2*-weighted imaging, such as susceptibility-weighted imaging (SWI), may be performed as part of the routine brain MRI examination and part of the full scan 12 for the platform 10. See Javier E. Villanueva-Meyer, MD, Marc C. Mabray, MD, and Soonmee Cha, MD *Current Clinical Brain Tumor Imaging Neurosurgery*. 2017 September; 81(3): 397-415, for an overview of current magnetic resonance imaging (MRI) methods routinely employed in the care of the brain tumor patient.

The primary roles of structural MRI in the initial brain tumor evaluation for the radiologist (and for the platform 10) include determining the lesion location, extent of tissue involvement, and resultant mass effect upon the brain, ventricular system, and vasculature. See *Review Update on brain tumor imaging*. Cha S Curr Neurol Neurosci Rep. 2005 May; 5(3):169-77. MRI offers superior soft tissue contrast over other cross-sectional imaging techniques allowing for better visualization of subtly infiltrated or disrupted parenchymal architecture. Furthermore, intravenous gadolinium-based contrast agents shorten T1 relaxation times and increase tissue contrast by accentuating areas where contrast agents have leaked out of the blood-brain barrier into the interstitial tissues, resulting in parenchymal enhancement. This breakdown of the blood-brain barrier is often a key visual feature seen in tumors as well as non-neoplastic conditions. See Neuwelt E A. *Mechanisms of disease: the blood-brain barrier*. Neurosurgery. 2004; 54(1): 131-142. See also Smirniotopoulos J G, Murphy F M, Rushing E J, Rees J H, Schroeder J W. *Patterns of contrast enhancement in the brain and meninges*. Radiographics. 2007; 27(2):525-551.

The platform 10 utilizes the same image interpretation "rules" used to train radiologists when interpreting images or scans 12 and these rules or guidelines are generally known in the art as outlined above. Within diffuse gliomas, contrast enhancement is positively correlated with tumor grade, although a few high-grade gliomas may show no or minimal enhancement and certain lower grade gliomas (World Health Organization [WHO] grade I) such as pilocytic astrocytoma or ganglioglioma can enhance avidly. The region of T2/FLAIR hyperintense signal abnormality surrounding the enhancing tumor core is typically referred to as peritumoral edema and can be vasogenic or infiltrative in nature. Vasogenic edema represents a reactive increase in extracellular water due to leakage of plasma fluid from altered tumor capillaries in the absence of tumor cells and is seen around intracranial metastases or non-infiltrative extra-axial tumors such as meningiomas. Infiltrative edema in gliomas represents a mixture of vasogenic edema and infiltrating tumor cells invading along, but not necessarily disrupting, white matter tracts and can be considered nonenhancing tumor owing to preserved integrity of the blood-brain barrier. See Stummer W. *Mechanisms of tumor-related brain edema*. Neurosurg Focus. 2007; 22(5):1-7. See also Nag S, Manias J L, Stewart D J. *Pathology and new players in the pathogenesis of brain edema*. Acta Neuropathol. 2009; 118(2):197-217. In fact, in many gliomas, the T2/FLAIR hyperintense signal abnormality from a visual review of a scan 12 alone may be indistinguishable from the primary mass lesion. See Ginsberg L E, Fuller G N, Hashmi M, Leeds N E, Schomer D F. *The significance of lack of MR contrast enhancement of supratentorial brain tumors in adults: histopathological evaluation of a series*. Surg Neurol. 1998; 49(4):436-440. See also Wen P Y, Macdonald D R, Reardon D A et al. *Updated response assessment criteria for high-grade gliomas: response assessment in Neuro-Oncology Working Group*. J Clin Oncol. 2010; 28(11):1963-1972.

Primary lesion location can help differentiate between tumor types. For example, extra-axial tumors such as meningiomas, schwannomas, and skull base tumors can generally, but not always, be differentiated from intra-axial tumors based on associated interposition of cerebrospinal fluid, vessels, or dura between the mass and cortex. See Drevelegas A. *Extra-axial brain tumors*. Eur Radiol. 2005; 15(3): 453-467. Similarly, the number of lesions is an important consideration as multiple lesions suggest metastatic disease or non-neoplastic processes such as demyelination, inflammation, or infection. See Cha S, Pierce S, Knopp E A et al. Dynamic contrast-enhanced T2*-*weighted MR imaging of tumefactive demyelinating lesions*. Am J Neuroradiol. 2001; 22(6):1109-1116. Finally, several imaging characteristics suggest tumor subtypes. The combination of a cyst and solid nodule within a tumor suggests brain tumors such as ganglioglioma, pilocytic astrocytoma, pleomorphic xanthoastrocytoma, and, in the posterior fossa, hemangioblastoma. See Raz E, Zagzag D, Saba L et al. *Cyst with a mural nodule tumor of the brain*. Cancer Imaging. 2012; 12(1):237-244. Calcifications can be seen in oligodendrogliomas, ependymomas, and pineal tumors, among others. See Tsuchiya K, Makita K, Furui S, Nitta K. *MRI appearances of calcified regions within intracranial tumours*. Neuroradiology. 1993; 35(5):341-344. Necrosis and hemorrhage are seen with higher grade gliomas, certain metastases, and rarely central nervous system (CNS) lymphoma in immunocompromised patients. See Kondziolka D, Bernstein M, Resch L et al. *Significance of hemorrhage into brain tumors: clinicopathological study*. J Neurosurg. 1987; 67(6):852-857. See also Rubenstein J, Fischbein N, Aldape K, Burton E, Shuman M. *Hemorrhage and VEGF expression in a case of primary CNS lymphoma*. J Neurooncol. 2002; 58(1):53-56.

Historically, brain tumors have been classified based on histology according to the WHO criteria. See Louis D N, Ohgaki H, Wiestler O D et al. *The* 2007 *WHO classification of tumours of the central nervous system*. Acta Neuropathol. 2007; 114(2):97-109. Diffuse gliomas are further subdivided into 4 grades by various histological features such as cellularity, nuclear atypia, mitotic activity, pleomorphism, vascular hyperplasia, and necrosis. Grade I gliomas including pilocytic astrocytoma, pleomorphic xanthoastrocytoma, and subependymal giant cell astrocytoma share a relatively benign biology with an indolent clinical course that is distinct from other diffuse infiltrating glioma grades. See Krishnatry R, Zhukova N, Guerreiro Stucklin A S et al. *Clinical and treatment factors determining long-term outcomes for adult survivors of childhood low-grade glioma: a population-based study*. Cancer. 2016; 122(8):1261-1269. See also Nageswara Rao A A, Packer R J. *Advances in the management of low-grade gliomas*. Curr Oncol Rep. 2014; 1 6(8):1-8. Grade II-IV gliomas are heterogeneous tumors with variable degrees of infiltration, atypia, and mitotic activity. Microvascular proliferation with endothelial hyperplasia and pseudopallisading necrosis are the defining histological hallmarks of grade IV gliomas, frequently referred to as glioblastomas. Insights into tumor biology have led to the identification of several molecular aberrations associated with genetic phenotypic differences in brain tumors. See *Cancer Genome Atlas Research Network Comprehensive genomic characterization defines human glioblastoma genes and core pathways*. Nature. 2008; 455(7216):1061-1068. See also Gupta K, Salunke P. *Molecular markers of glioma: an update on recent progress and perspectives*. J Cancer Res Clin Oncol. 2012; 138(12):1971-1981.

From the above detailed discussion it is clear that the platform 10, like the radiologist, uses more than merely pixel/voxel color differentiation (or edge and contrast values) in tumor identification. The next step in providing an effective and efficient precision artificial intelligence based neuroradiology platform 10 for neurological tumor identification is supervised learning 15 of the platform 10 on a dataset. The aim of supervised, machine learning 15 is to build a network on the platform 10 that makes predictions based on evidence in the presence of uncertainty. As the adaptive algorithms of the platform 10 identify patterns in data, the platform "learns" from the observations. When exposed to more observations, the platform 10 improves its predictive performance. The supervised learning 15 is defined as classification, as the goal of the platform 10 is to assign a label (or class) 17 from a finite set of classes to an observation. That is, responses of the platform 10 are categorical variables. Specifically the platform 10 is configured to classify the tissue within the "classification voxels" 25 of a specific given data set. The classification or label 17 in the broadest context of the invention may merely be a binary choice of "normal tissue" or "tumor". FIG. 2 is an exploded schematic view of a scan 12 used by the artificial intelligence based neuroradiology platform 10 for neurological tumor identification with representative classification voxels 25 on the scan and assigned classification labels 17 for the classification voxels 25 in accordance with one aspect of the present invention.

The classification labels 17 for classification voxels 25 may be expanded to include tumor identification and identification of other tissue structure (e.g., grey matter, dura layer, arterial flow, lesions, venous tissue, skull, tumor type, etc.). As detailed above the MRI scans 12 can be utilized to identify specific tumor types and other physiologic structures useful to the clinician, and the platform 10 may be utilized to provide such identification. Specifically, the platform 10 can be used to identify and label 17 the type of tumor (e.g. a metastatic brain cancer tumor, or a metastatic breast brain cancer tumor), as well as the specific tissue identifications. Distinguishing between blood supply features and tumor edges, for example, can greatly aid in treatment options for a patient. The platform 10 has the ability to track and incorporate large numbers of variables (biomarkers) that can be used or be useful to make these distinctions for labels 17. As a comparison, it becomes highly labor intensive or simply impossible for the radiologist to make similar determinations in a practical manner.

The classification voxels 25 are at least equal to, or generally larger than the resolution voxels. Typically, a plurality of resolution voxels form a classification voxel 25. In the supervised training of the platform 10 the classification voxels 25 for training will be at least 5 times and preferably at least 10 times the resolution voxel size, and most preferably at least 20 times the resolution voxel size. In practice the classification voxels 25 used in training were cubes of 31 mm per side, which is a size that is more than sufficient for identification of medium sized tumor.

The keys to the training data set used in training in the supervised learning 15 is that the classification voxels 25 for each full scan will all be identified or labeled 30 to provide a ground truth for the supervised learning 15. Typically these will be training scans provided by, or proofed by, a radiologists in which each classification voxel 25 of the training set is properly identified or labeled 30 by the radiologist. Known labels 30 for the training set represent the ground truth or known values that the platform 10 is training upon or towards, and the desire for the platform 10 is that the predicted labels for each classification voxel 25 provided by the platform 10 matches known labels 30 for each classification voxel 25 of the training set. In practice, as shown in the figures, the labels 30 of the training set may only be of the classification voxels 25 that are out of the ordinary, wherein only "tumor" labels 30 are physically listed by the radiologist and the remaining unnoted classification voxels 25 are "normal tissue". Even if a larger number or set of labels are provided for use in a given review, the most commonly occurring label (such as "normal tissue") can be left unmarked in the training set as a default.

The training set must include a statistically significant number of distinct full scans (or separate patients). At least 40 full scans is believe to provide a statistically significant training set, although greater numbers will yield better training for the platform. Preferably at least 60 full scans are used, and more preferably at least 100 full scans are used in training 15. In one implementation of the present invention 139 full scans was used in the supervised learning 15 with the classification being limited to "normal tissue" and "tumor".

In the supervised learning 15, for each full scan 12 the multilayer convolutional network for neurological tumor identification of the platform 10 segments the data set into resolution voxels (after cropping to region of interest) and will classify each classification voxel 25 with a label 17 (e.g. "normal tissue" or "tumor") based upon the network rules of the platform 10. The classification voxel 25 for training is made up of multiple resolution voxels and the platform 10 may label subcomponents of the classification voxel 25 with labels (e.g. venous subcomponents, grey matter subcomponents, etc.) that are collectively evaluated to determine the predicted label 17 for the classification voxel 25. The predicted label 17 for each classification voxel 25 is compared with the ground truth label 30 for the classification voxel 25 provided by the training set (provided by the radiologist) and the platform 10 is modified (learns) accordingly.

Figure 6A:
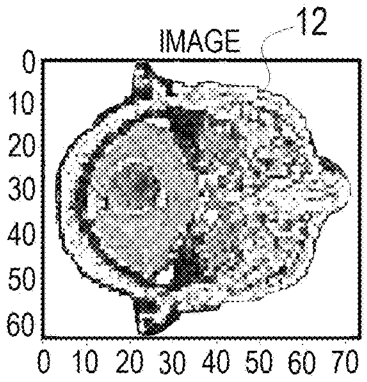
Figure 6B:
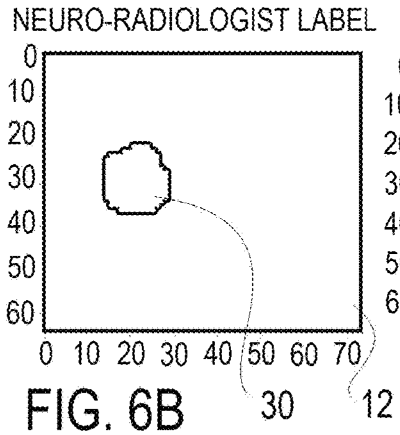
Figure 6C:
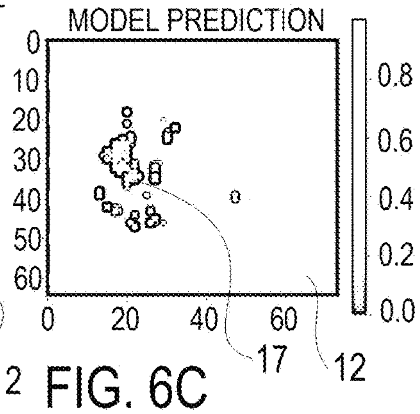

FIG. 3A is schematic view of a training scan 12 with known classification labels 30 for training the artificial intelligence based neuroradiology platform 10 for neurological tumor identification of the present invention. FIG. 3B is schematic view of a scan 12 associated with training scan 12 of FIG. 3A with predicted classification labels 17 by the artificial intelligence based neuroradiology platform 10 for neurological tumor identification of the present invention and FIG. 3C is a superimposed view of FIGS. 3A and 3B;

FIGS. 4A, 5A and 6A are schematic views of distinct training scans 12 for training the artificial intelligence based neuroradiology platform 10 for neurological tumor identification of the present invention; and FIGS. 4B, 5B and 5C are schematic views of the training scans 12 of FIGS. 4A, 5A and 6A, respectively, with added known classification labels 30 for training the artificial intelligence based neuroradiology platform 10 for neurological tumor identification of the present invention. FIGS. 4C, 5C and 6C are schematic view of scans 12 associated with training scan 12 of FIGS. 4A, 5A and 6A, respectively, with predicted classification labels 17 by the artificial intelligence based neuroradiology platform 10 for neurological tumor identification of the present invention;

Following supervised learning is validation 35 of the platform 10 of the present invention, wherein validation 35 of classification of tissue within classification voxels 25 of a specific given validation data set by the multilayer convolutional network for neurological tumor identification of the platform 10 provides that each classification voxel 25 of the validation data set has a predetermined ground truth. The validation 35 of the platform 10 operates similar to training or supervised learning 15, but for a different purpose. The validating dataset of the validation 35 can typically be less distinct scans or patients than the training data set used in the supervised learning 15, such as 10-20 scans. The validating dataset will also have ground truth labels 30 for the classification voxels 25, but these labels 30 are primarily used to evaluate the performance of the platform 10 rather than train the platform 10.

Figure 7:
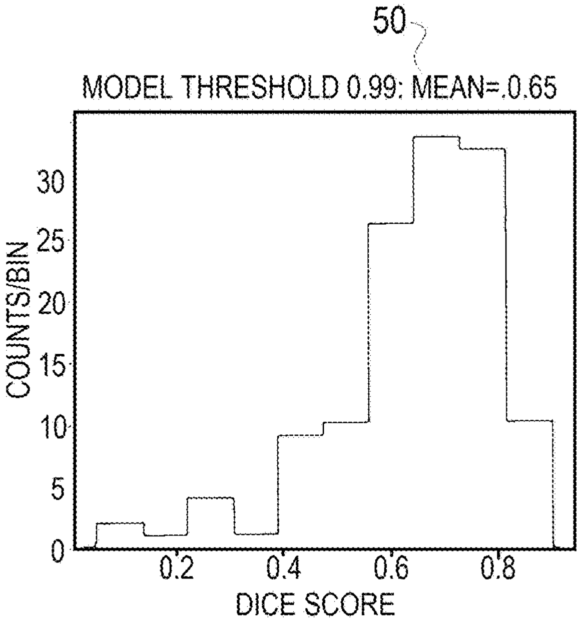
FIG. 7 is a graph of a Sørensen-Dice coefficient or Dice Score for the artificial intelligence based neuroradiology platform for neurological tumor identification of the present invention.
Figure 8:
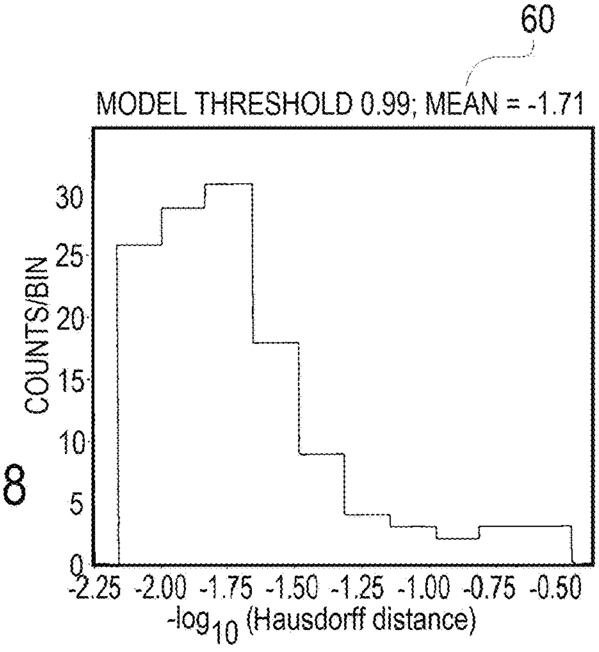
FIG. 8 is a graph of a Hausdorff distance for the artificial intelligence based neuroradiology platform for neurological tumor identification of the present invention.

The validation 35 results in a standard measuring metric like a Dice score or Sørensen-Dice coefficient 50 shown in FIG. 7 or a Hausdorff distance 60. The Sørensen-Dice coefficient or simply Dice Score (known by many monikers) is a statistic used to gauge the similarity of two samples and is a quotient of similarity and ranges between 0 and 1. The Sørensen-Dice coefficient was independently developed by the botanists Thorvald Sørensenand and Lee Raymond Dice, who published in 1948 and 1945 respectively. The Dice Score 50 has been commonly used in image segmentation, in particular for comparing algorithm output against reference masks in medical applications. See Zijdenbos, A. P.; Dawant, B. M.; Margolin, R. A.; Palmer, A. C. (1994). *Morphometric analysis of white matter lesions in MR images: method and validatio*". IEEE Transactions on Medical Imaging. Institute of Electrical and Electronics Engineers (IEEE). 13 (4): 716-724. The Hausdorff distance 60 is used to measure the difference between two different representations of the same 3D object particularly when generating level of detail for efficient display of complex 3D models. See Cignoni, P.; Rocchini, C; Scopigno, R. (1998) *Metro: Measuring Error on Simplified Surfaces*. Computer Graphics Forum 17 (2): 167-174. A successful validation of the platform 10 is a mean Dice Score 50 greater than 0.60 or an absolute value of a mean Hausdorff distance 60 of greater than 1.50 (log scale) or less than −1.50 (log scale). The platform 10 in initial results had a mean Dice Score of 0.65 and a mean Hausdorff distance 60 of −1.71.

Following validation 35 to obtain the scores for the platform 10 on standardized measurements, the ground truth labels 30 of the validation data set can be used to further train the platform 10 in the same manner as the supervised learning 15 above, such that validation 35 can further improve effectiveness of the platform 10. The supervised learning 15 and validation 35 can be combined effectively in one step with a final testing subset of the training dataset used for validation 35. The validation 35 may, of course, be different than the training of supervised learning 15, which allows for the size of the classification voxel 25 used in the validation 35 to differ than that used in training, typically smaller, but still typically about 5 to 20 times the resolution voxel size (e.g., cubes of 5, 10 or 20 mm). The possible smaller size for the classification voxel 25 in the validation 35 step compared with supervised learning 15 step is because of the smaller number of individual scans 12 needed in a validation data set and thus the less total time (and cost) associated with preparing accurate validation data sets. The size of the classification voxel 25 used in the validation 35 is equal to or smaller than the classification voxel 25 size used by the platform 10 in practice or implementation 55. The classifications or labels 17 for each voxel 25 (e.g. tumor, normal tissue, or specific tumor type or specific tissue type) used in the validation must be of equal or greater detail than that used by the platform 10 in practice.

Unsuccessful validation 35 of a platform 10 can be cured with further supervised learning 15 and or supplemental rules added to the network outside of a supplemental to the supervised learning 15.

Following successful validation the platform 10 may be used in practice by practitioners, known as platform implementation 55. The clinician or technician selects the desired size of the classification voxels 25 that are equal to or greater than those used in validation 35, but generally equal thereto. The clinician or technician selects the desired labels 17 (or set of labels 17) for the classification voxels 25 that are the same as or less complex (more generic) than those used in validation 35, but generally equal in complexity to the validation labels 17. For each full patient scan 12 the multilayer convolutional network for neurological tumor identification of the platform 10 segments the data set into resolution voxels (after cropping to region of interest) and will classify each classification voxel 25 with a label 17 (e.g. "normal tissue" or "tumor" or other accepted label) based upon the network rules of the platform 10.

The platform 10 can receive further learning based upon any ground truth or known feedback it receives. For example the platform 10 should be capable of receiving confirmation of or correction of any label 17 of any classification voxel 25 for any data set. In accordance with the recommendations of the Radiological Society of North America (RSNA), the American College of Radiology (ACR), and The Academy for Radiology and Biomedical Imaging Research (The Academy) the platform 10 is configured and designed for stand-alone distributed training to reduce the need for data exchange between institutions, however communication between separate platforms 10 can allow for an exchange of known "ground truths" of each platform 10 in co-operative co-training. This co-training may be in the form of training updates sent to all platforms 10 in the field, based upon ground truths from a distributed collection of platforms 10 that are uploaded to a central location. The platform 10 is set up for stand-alone operation, but this co-operative improvement of the network of each platform 10 is disclosed as possible.

The platform 10 is preferably trained to distinguish tumors from blood vessels within the brain which can appear similar in the 3D images. The platform 10 provides an automated tool that can reliable segment tumors immediately after MRI acquisition and easily be integrated into neuro-navigation software, such as available commercially from, for example Medtronic. The uniqueness of platform 10 is, in part, the ability to process large datasets of patient scans 12 and to segment and identify quickly relevant and non-relevant surgical areas associated with tumors with probability that is higher than currently exists. The platform 10 may reside on a distinct operating system such as a dedicated computer, or further may be implemented on a dedicated chipset wherein the speed and processing is only limited by chipset not the algorithm. This platform 10 can be applied to all aspects of tumor identification. The platform 10 may be accessible by operators and vendors via conventional coupling including internet connection.

According to the Precision Medicine Initiative, precision medicine is "an emerging approach for disease treatment and prevention that takes into account individual variability in genes, environment, and lifestyle for each person." A precision medicine approach allows doctors and researchers to predict more accurately which treatment and prevention strategies for a particular disease will work in which groups of people. It is in contrast to a one-size-fits-all approach, in which disease treatment and prevention strategies are developed for the average person, with less consideration for the differences between individuals. Although the term "precision medicine" is relatively new, the concept has been a part of healthcare for many years. For example, a person who needs a blood transfusion is not given blood from a randomly selected donor; instead, the donor's blood type is matched to the recipient to reduce the risk of complications. Within the meaning of this application the phrase precision medical treatment will represent medical treatment that takes into account at least one aspect of an individual's genes, environment and lifestyle. The platform 10 can model the tumor with rules that take into account at least one aspect of an individual's genes, environment and lifestyle to provide precision medical treatment.

The updated WHO classification incorporates molecular markers along with histology and defines specific entities on the basis of IDH mutation and 1p19q chromosomal deletion. See Louis D N, Perry A, Reifenberger G et al. *The* 2016 *World Health Organization Classification of Tumors of the Central Nervous System: a summary*. Acta Neuropathol. 2016; 131(6):803-820. These, along with other molecular markers including p53, RB1, EGFR, PTEN, MGMT, BRAF, ATRX, TERT, and histone H3, represent a nosological shift where histopathological phenotype is complemented by molecular genetic phenotype to better classify brain tumors and predict their clinical behavior. See Mabray M C, Barajas R F Jr, Cha S. *Modern brain tumor imaging*. Brain Tumor Res Treat. 2015; 3(1):8-16. MRI is rapidly catching up with these genetic advances and helping to noninvasively explore the link between the molecular genetic basis of glioma biology and the imaging characteristics of their morphological phenotypes. The platform 10 of the present invention can incorporate such molecular markers in its evaluation, if they are known, to expand the uses and application for the platform 10.

Patients being treated with radiation for a tumor, a brain tumor, will often display a pseudo image on a conventional scan (CT or MRI) with biomarkers that can be indicative of tumor growth and there are also biomarkers indicating these are false markers of tumor growth. The presence of false markers of tumor growth on an image is an opportune time to introduce T-cell/begin TC therapy. The AI based image processing platform 10 can identify such pseudo images and use such indication as timely initiating T-cell therapy in Post radiation patients as well accurately defining the margins for such therapy in use. The AI based image processing platform 10 can thus efficiently initiate T-cell therapy and track ongoing T-cell therapy.

The above described platform 10 provides a medical assist neurological predictive modeling platform utilizing artificial intelligence based 3D image analysis predicting tumors within the brain and the spine. Within this application, precision medicine uses specific information about a person's tumor to help diagnose, plan treatment, find out how well treatment is working, or make a prognosis.

As discussed above, if require the platform 10 can use a series of 2D images wherein the platform 10 a model prediction for each 2D image, which can be used to map out a prospective or suspected tumor in 3D by sequencing through all 2D slices to assemble the 3D image or model.

The above described representative example platform evidences the efficacy of a brain and spine tumor predictive modeling platform utilizing artificial intelligence based analysis utilizing 2D and 3D imaging analysis. The brain tumor imaging platform 10 as discussed above preferably includes arterial and venous traceability of tumor and offsets, along with tumor differentiation. The combination of arterial and venous traceability of tumor and offsets, along with tumor differentiation is believed to provide substantial utility to the subject platform 10.

Diabetes Precision Medical Treatment Predictive Modeling Platform

The present invention according to a further distinct aspect of the invention yields a precision medical treatment predictive modeling platform for diabetes patients. The system predicts a patient's ability to process various classes of diabetic drugs based upon genetic variations—statin analysis. The platform of this aspect of the present invention may be described as a Pharmacogenomics platform. Pharmacogenomics is a part of precision medicine. Pharmacogenomics is the study of how genes affect a person's response to particular drugs. This relatively new field combines pharmacology (the science of drugs) and genomics (the study of genes and their functions) to develop effective, safe medications and doses that are tailored to variations in a person's genes.

Diabetes Mellitus (DM) is defined as a group of metabolic disorders mainly caused by abnormal insulin secretion and/or action. Insulin deficiency results in elevated blood glucose levels (hyperglycemia) and impaired metabolism of carbohydrates, fat and proteins. DM is one of the most common endocrine disorders, affecting more than 200 million people worldwide. The onset of diabetes is estimated to rise dramatically in the upcoming years. DM can be divided into several distinct types. However, there are two major clinical types, type 1 diabetes (T1D) and type 2 diabetes (T2D), according to the etiopathology of the disorder. T2D appears to be the most common form of diabetes (90% of all diabetic patients), mainly characterized by insulin resistance. The main causes of T2D include lifestyle, physical activity, dietary habits and heredity, whereas T1D is thought to be due to autoimmunological destruction of the Langerhans islets hosting pancreatic-B cells. T1D affects almost 10% of all diabetic patients worldwide, with 10% of them ultimately developing idiopathic diabetes. Other forms of DM, classified on the basis of insulin secretion profile and/or onset, include Gestational Diabetes, endocrinopathies, MODY (Maturity Onset Diabetes of the Young), neonatal, mitochondrial, and pregnancy diabetes. The symptoms of DM include polyurea, polydipsia, and significant weight loss among others. Diagnosis depends on blood glucose levels (fasting plasma glucose=7.0 mmol/L).

DM progression is strongly linked to several complications, mainly due to chronic hyperglycemia. It is well-known that DM covers a wide range of heterogeneous pathophysiological conditions. The most common complications are divided into micro- and macro-vascular disorders, including diabetic nephropathy, retinopathy, neuropathy, diabetic coma and cardiovascular disease. Due to high DM mortality and morbidity as well as related disorders, prevention and treatment attracts broad and significant interest. Insulin administration is the main treatment for T1D, although insulin is also provided in certain cases of T2D patients, when hyperglycemia cannot be controlled through diet, weight loss, exercise and oral medication. Current medication targets primarily a) saving one's life and alleviating the disease symptoms, and b) prevention of long term diabetic complications and/or elimination of several risk factors, thereby increasing longevity. The most common anti-diabetic agents include sulfonylurea, metformin, alpha-glucosidase inhibitor, peptide analogs, non-sulfonylurea secretagogues, etc. The majority of the present anti-diabetic agents, however, exhibit numerous side-effects. In addition, insulin therapy is related to weight gain and hypoglycemic events. Hence, anti-diabetic drug design and discovery is of great concern and concurrently a research challenge.

Although extensive research in DM has provided significant knowledge, over the past decades, on the a) etiopathology (genetic or environmental factors and cellular mechanisms), b) treatment, and c) screening and management of the disease, there is still much to be discovered, unraveled, clarified and delineated. Through such processes, diagnosis, prognostic evaluation of appropriate treatment and clinical administration could gain significant ground toward medical handling of the disease. In such an effort, reliance on a large and fast increasing body of research and clinical data serves to establish a significant basis for safe diagnosis and follow-up treatment. Thus, data mining and machine learning emerge as key processes, contributing decisively to the decision-making clinician. The aspiration, therefore, is to link data assessment to diagnosis and appropriate decision-making in drug administration.

One aspect of this embodiment of the present invention provides construction of a representative sample diabetes predictive modeling platform utilizing artificial intelligence based analysis predicting glucose levels based upon historical measurements. A representative platform utilized data taken from 70 datasets of diabetics containing ~several months of data including: Glucose measurements (and relative meal information); Insulin doses (3 different types), notes regarding the onset of hypoglycemic symptoms. In this platform measurements were binned into 4 hour time intervals and the platform successfully predicted glucose level in four hours based upon the past 48 hours of measurement. The platform training data was grouped into 12 entries sequences (12 entries×4 hours/entry=48 hours) and the actual next true glucose measurement. The platform was trained based upon long short-term memory units on these sequence and label pairs.

Figure 9:
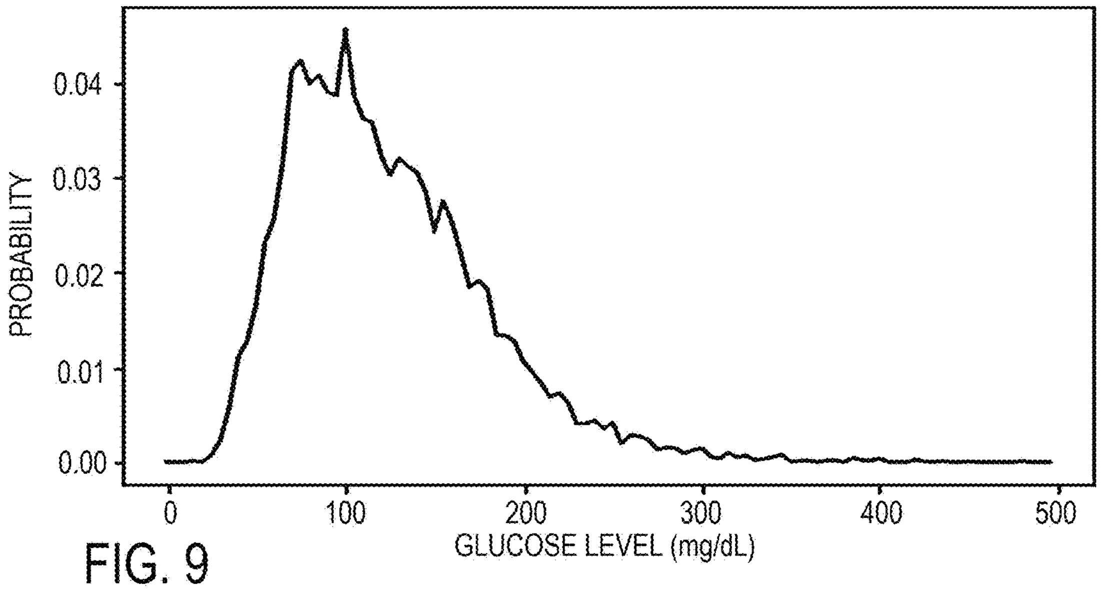
FIG. 9 is a graph of outputs a probability distribution of the next glucose value in the sequence for a diabetic related platform according to one aspect of the invention.
Figure 10:
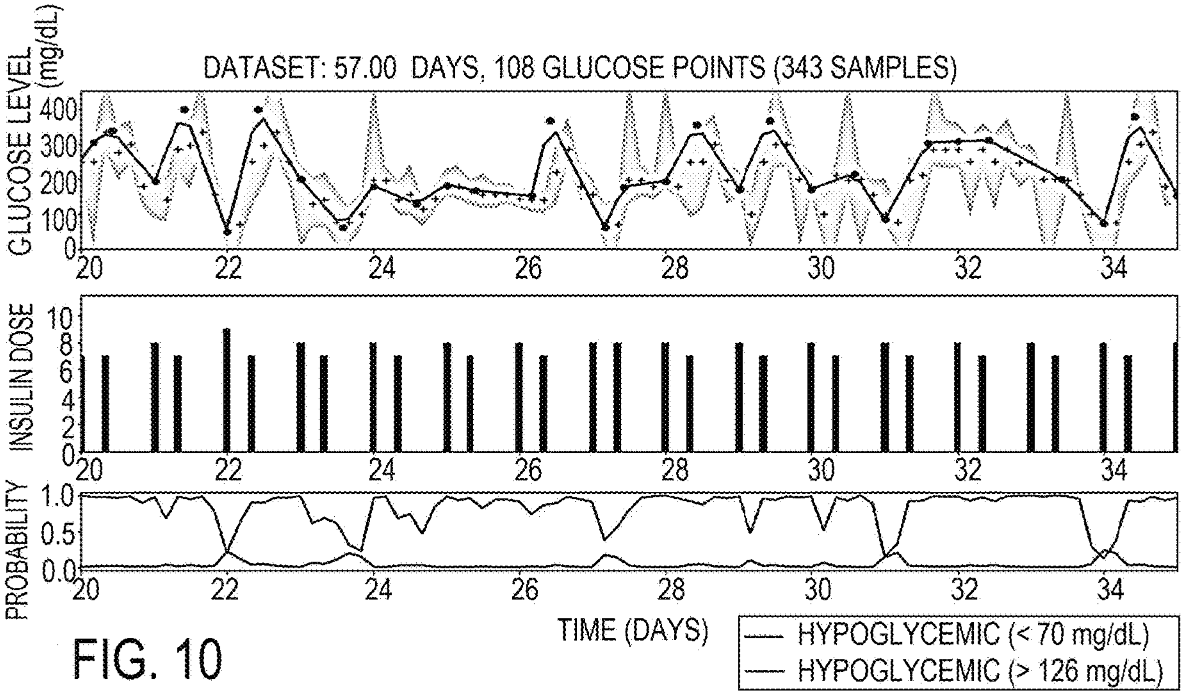
FIG. 10 shows the recorded data and the prediction with a prediction range for a diabetic platform of the present invention.

The representative platform outputs a probability distribution of the next glucose value in the sequence (binned in steps of 5 mg/dl), a representative sample of which appears as FIG. 9:

FIG. 10 shows the recorded data and the prediction with a prediction range for the platform of the present invention, wherein dots are recorded values, crosses are predicted values, the shaded area is the 50% prediction range and the line shows the interpolated data.

The platform can improve results with data sets covering the same time intervals and measurements at a common time, and further separating the subject by type of insulin. The platform will yield better efficiencies where concentrating on shorter time frames. Additionally it is believed that the platform may be utilized or trained on a specific patient for the optimal results for a given patient. The diabetes model platform described above was using cohorts already diseased, however the application of this model platform as described would analogously predict illness in "healthy" or undiagnosed cohorts.

The above described representative example platform evidences the efficacy of a diabetes predictive modeling platform utilizing artificial intelligence based analysis predicting glucose levels based upon historical measurements.

Precision Medical Treatment Predictive Modeling Platform for Cardiopulmonary Analysis Another aspect of the present invention provided predictive modeling platform utilizing artificial intelligence based 3D image analysis similar or analogous to that described above but configured for predicting likely Transcatheter Aortic Valve Implantation or Tavi candidates and/or predicting Tavi results as well as add predictability of valve leaflet size and valve sizes. Such a modification of the platform 10 would include genetic background for patients, such as phenal subgroups.

Transcatheter Aortic Valve Implantation is a procedure that helps to improve a damaged aortic valve. During a TAVI procedure, an artificial valve made of natural animal heart tissue (usually from a cow or a pig) will be implanted into the patient's heart. TAVI is a minimally invasive procedure that helps give the patient a better chance of recovering quicker after surgery. However, as with any procedure, there are some risks associated with a TAVI. The known risks can include: Bleeding or vascular injury, Abnormal heart rhythms (arrhythmias)—sometimes requiring pacemaker, Obstructed coronary artery, Aortic regurgitation, Kidney impairment, Stroke and even Death. The predictive modeling platform of the present invention may utilize artificial intelligence based 3D image analysis of the prospective patients heart analogous to that described above together with and genetic background to predict the risks of known complications within a range of likelihoods (50% predictive range) for identifying likely Tavi candidates and/or predicting Tavi results including an added predictability of valve leaflet size and valve sizes. As with other platforms discussed above the platform is trained on known datasets of past results.

Although the present invention has been described with particularity herein, the scope of the present invention is not limited to the specific embodiment disclosed. For example, another aspect of the invention provides a cardiopulmonary predictive modeling platform utilizing artificial intelligence based 3D image analysis similar to that described above but that will identify commonly missed diagnosis in the acute cardiopulmonary areas including pulmonary embolism, penetrating atherosclerotic ulcer, and venothromboembolism. Alternatively, the present invention may be utilized as predictive analytics for computer vision application for Dentistry Cavities, Gum Disease, Root Canal using the methodologies outlined above.

It will be apparent to those of ordinary skill in the art that various modifications may be made to the present invention without departing from the spirit and scope thereof. The scope of the present invention should be defined by the appended claims and equivalents thereto.

What is claimed is:

1. A method of implementing an artificial intelligence based imaging platform for neurological analysis comprising the steps of:

A) providing a validated multilayer convolutional network for neurological analysis configured for segmenting data sets of neurological scans into resolution voxels, wherein the resolution voxels are representative of a smallest volumetric region within which the platform can segment the data sets of neurological scans, wherein a prior validation of the validated multilayer convolutional network includes i) defining classification voxels of a training data set which are representative of volumetric regions, wherein each classification voxel of the training data set is made up of one or more resolution voxels, ii) supervised learning of the platform by classification of tissue within said classification voxels of the training data set by the multilayer convolutional network for neurological analysis being validated with each classification voxel of the training data set having a predetermined ground truth, iii) validating the classification of tissue within said classification voxels of the validation data set by the multilayer convolutional network for neurological analysis being validated with each classification voxel of the validation data set having a predetermined ground truth; and B) implementing the validated multilayer convolutional network by classification of neurological tissue within classification voxels of at least one patient data set by the validated multilayer convolutional network for neurological analysis with each classification voxel of the at least one patient data set assigned a label, wherein the implementing the validated multilayer convolutional network includes at least one of i) mapping neurologic tissue and ii) mapping of a neurological tumor of a patient.

2. The method of implementing the artificial intelligence based imaging platform for neurological analysis according to claim 1, wherein the platform further includes performing weighted imaging on the at least one patient data set.

3. The method of implementing the artificial intelligence based imaging platform for neurological analysis according to claim 2, further including utilizing long short-term memory units for the weighted imaging.

4. The method of implementing the artificial intelligence based imaging platform for neurological analysis according to claim 3, wherein a clinician can set a size of the classification voxels of the at least one patient data set.

5. The method of implementing the artificial intelligence based imaging platform for one of neurological or cardiopulmonary analysis according to claim 4, wherein the classification voxels of the at least one patient data are at least 5 times larger than the smallest volumetric region.

6. The method of implementing the artificial intelligence based imaging platform for neurological analysis according to claim 3, wherein the classification voxels of the at least one patient data set are at least 5 times larger than the smallest volume region and wherein the smallest volume region is a cube of 1 mm.

7. The method of implementing the artificial intelligence based imaging platform for neurological analysis according to claim 2, wherein the platform is configured for mapping the neurologic tissue.

8. The method of implementing the artificial intelligence based imaging platform for neurological analysis according to claim 7, wherein a clinician can set a size of the classification voxels of the at least one patient data set.

9. The method of implementing the artificial intelligence based imaging platform for neurological analysis according to claim 7, wherein the classification voxels of the at least one patient data are at least 5 times larger than the smallest volumetric region.

10. The method of implementing the artificial intelligence based imaging platform for neurological analysis according to claim 2, wherein the platform is configured for mapping of the neurological tumor of the patient.

11. The method of implementing the artificial intelligence based imaging platform for neurological analysis according to claim 10, wherein a clinician can set a size of the classification voxels of the at least one patient data set.

12. The method of implementing the artificial intelligence based imaging platform for neurological analysis according to claim 10, wherein the classification voxels of the at least one patient data are at least 5 times larger than the smallest volumetric region.

13. The method of implementing the artificial intelligence based imaging platform for neurological analysis according to claim 2, wherein the platform is further configured for mapping neurological blood vessels of a patient.

14. The method of implementing the artificial intelligence based imaging platform for neurological analysis according to claim 13, wherein a clinician can set a size of the classification voxels of the at least one patient data set.

15. The method of implementing the artificial intelligence based imaging platform for neurological analysis according to claim 13, wherein the classification voxels of the at least one patient data are at least 5 times larger than the smallest volumetric region.

16. The method of implementing the artificial intelligence based imaging platform for neurological analysis according to claim 2, wherein a clinician can set a size of the classification voxels of the at least one patient data set.

* * * * *